United States Patent [19]

Szuszkiewicz

[11] Patent Number: 5,163,907

[45] Date of Patent: Nov. 17, 1992

[54] SINGLE USE RETRACTABLE NEEDLE SYRINGE

[76] Inventor: Christine M. Szuszkiewicz, 2401 Tunlaw Rd., NW., Washington, D.C. 20007

[21] Appl. No.: 720,208

[22] Filed: Jun. 24, 1991

[51] Int. Cl.⁵ .............................................. A61M 5/00
[52] U.S. Cl. .................................... 604/110; 604/195
[58] Field of Search ............... 604/110, 195, 192, 198, 604/263, 218, 187

[56] References Cited

U.S. PATENT DOCUMENTS

| | | | |
|---|---|---|---|
| 4,026,287 | 5/1977 | Haller. | |
| 4,692,156 | 9/1987 | Haller | 604/195 |
| 4,710,170 | 12/1987 | Haber et al. | 604/110 |
| 4,790,822 | 12/1988 | Haining | 604/110 |
| 4,804,370 | 2/1989 | Haber et al. | 604/195 |
| 4,826,484 | 5/1989 | Haber et al. | 604/110 |
| 4,838,869 | 6/1989 | Allard et al. | 604/195 |
| 4,874,382 | 10/1989 | Lindemann et al. | 604/195 |
| 4,883,471 | 11/1989 | Braginetz et al. | 604/195 |
| 4,888,002 | 12/1989 | Braginetz et al. | 604/195 |
| 4,921,486 | 5/1990 | DeChellis et al. | 604/110 |
| 4,932,939 | 6/1990 | Magre et al. | 604/110 |
| 4,935,015 | 6/1990 | Hall | 604/195 |
| 4,950,241 | 6/1990 | Ranford | 604/195 |
| 4,955,870 | 9/1990 | Ridderheim et al. | 604/195 |
| 4,969,877 | 11/1990 | Kornberg | 604/195 |
| 4,973,316 | 11/1990 | Dysarz | 604/195 |
| 4,986,813 | 1/1991 | Blake et al. | 604/110 |
| 4,995,874 | 2/1991 | Strickland | 604/195 |
| 5,000,738 | 3/1991 | LaVallo et al. | 604/110 |
| 5,026,354 | 6/1991 | Kocses | 604/195 |

FOREIGN PATENT DOCUMENTS

957829  2/1950  France ................................ 604/218

Primary Examiner—John D. Yasko
Attorney, Agent, or Firm—Keil & Weinkauf

[57] ABSTRACT

A hypodermic syringe made up of a retractable needle assembly, a barrel, and a plunger. The needle assembly and the barrel are attached in such a way that they may be separated and the plunger and the needle assembly are adapted to be secured together. When the plunger is pushed all the way forward, the plunger and the needle assembly become secured to each other. When the plunger is pulled back, the needle is retracted. The needle assembly or the plunger and the barrel each have interlocking securing mechanisms to affix the needle assembly near the proximal end of the barrel. The mechanisms prevent the removal of the retracted needle assembly from the barrel. Thus, the syringe is not reusable and provides protection against accidental needlesticks. The syringe may have a compressible rubber collar around the tip of the plunger to provide for selective engagement of the plunger to the needle assembly and to expel all the fluid contents of the syringe.

13 Claims, 8 Drawing Sheets

SINGLE USE RETRACTABLE NEEDLE SYRINGE

BACKGROUND OF THE INVENTION

1. Field of the Invention

This invention pertains to a cross-infection-prevention medical device. More particularly, it pertains to an infection prevention syringe which has a retractable needle assembly that protects patients and medical workers from disease or injury due to reuse or accidental contact with the needle.

In 1987 the first lawsuit arose as the result of a healthcare worker contracting AIDS on the job. The unfortunate doctor contracted the disease after accidentally sticking herself with a needle after giving an AIDS patient an injection. The patient's blood was on the needle and was transferred to her body via the needlestick injury.

Over 20 different pathogens have been documented as being transferred from patient to healthcare worker by needlestick injuries. Over 12,000 become infected with and nearly 300 workers die annually from hepatitis B contracted on the job.[1] Studies have shown that 17 percent of needle-stick injuries occur during use of the syringe, 70 percent occur when the user prepares the device for disposal, and 13 percent occur during or after disposal. Overall, one third of injuries occur during recapping of the device.[2] ,6 1. Jagger, Janine. Rates of Needle-Stick Injury Caused by Various Devices in a University Hospital. New England Journal of Medicine. Aug. 4, 1988, p. 284. ,6 2. Ibid.

2. Description of Related Art

In many countries, medical workers reuse disposable syringes, even though they know they should not, because of a lack of adequate healthcare supplies. Epidemics have been caused in hospitals by this practice, as patients are contaminated by needles used on other patients. In the majority of cases, it would be better for the patient to receive no medication than for them to receive medication and be infected with a life-threatening disease. Similar problems result from the reuse of syringes by drug abusers.

U.S. Pat. No. 4,710,170 to Haber et al discloses a disposable, anti-needle strike and anti-drug-abuse syringe. The syringe includes a conventional hypodermic needle and luer lock assembly which is connected to and supported from a needle carrier base. The needle carrier base is removably attached to a first end of the syringe cylinder, such that the needle projects outwardly therefrom for injecting a fluid from the cylinder in the conventional manner.

The syringe also includes a piston assembly comprising the detachable connection of an elongated piston stem to a seal and lock assembly. A torroidal seal, formed at one end of the seal and lock assembly, functions as a plunger when the piston assembly is moved axially through the syringe cylinder during a fluid injection procedure. The torroidal seal has a receptacle formed therein at which the seal and lock assembly is adapted to selectively engage the needle carrier base when the piston assembly is moved to the first end of the syringe cylinder. The piston assembly is then moved away from the first cylinder end, whereby to remove the needle carrier base and the attached hypodermic needle from the first to an opposite end of the cylinder. The needle carrier base is anchored at the opposite cylinder end, such that the hypodermic needle extends into and is shielded by the syringe cylinder. The piston stem is detached from the piston assembly by bending the stem relative to the seal and lock assembly. The piston stem is then inserted through an orifice at the first end of the syringe cylinder from which the needle carrier base was previously removed. The stem is axially advanced through the interior of the syringe cylinder towards the opposite end thereof until contact is made with the needle cannula at the interior of the cylinder. The impact of the piston stem against the needle cannula bends, rather than breaks, the needle within the cylinder. The piston stem is locked in its final position within the syringe cylinder to prevent access to or contact with the needle. The syringe may then be discarded in a normal fashion. The resulting cartridge is rendered safe by locking the hypodermic needle and needle carrier base within the syringe cylinder, so that the needle is shielded by the syringe cylinder.

U.S. Pat. No. 4,710,170, the Haber invention, causes waste of medication due to the amount of "dead space" in the design; medication is not completely expelled from the recesses which remain after the plunger has been pushed to the distal end of the syringe. In addition, the Haber invention can be reassembled; the parts can be separated from each other, and the "needle carrier base" can be refixed in place at the end of the syringe permitting reuse of the syringe. Furthermore, the needle assembly is rendered non-reusable only if the user chooses to destroy it, and if the user does choose to do so it will require extra effort and time. The Haber invention necessitates the attaching of a plunger to a separate "seal and lock assembly" before the syringe may be used, a step requiring more assembly and more room for quality problems.

The Hall invention, described in U.S. Pat. No. 4,935,015 requires that the needle be attached to the syringe barrel by being inserted through the proximal opening of the syringe barrel and being screwed into place at the distal end of the syringe. The plunger is used to push the needle up into place through the syringe barrel and to screw it in place. The plunger must then be pulled out of the needle base. This process is time consuming and leaves much opportunity for the needle to be contaminated and for the user to stick him or herself with the unused needle.

The device disclosed by Haining in U.S. Pat. No. 4,790,822 could be broken down and reassembled for reuse. In addition, prior to initial use, the top or the T-type head could be cut off to deactivate the mechanism which makes the syringe non-reusable. In addition, the user must break off the plunger to prevent the needle from accidentally being pushed out of the barrel after use, requiring extra time and effort and potentially causing a jolting movement of the syringe which would lead blood to splatter from the end of the syringe.

SUMMARY OF THE INVENTION

The present invention is intended to provide a quick, easy-to-use, reliable and inexpensive needlestick and reuse prevention syringe.

The products are designed to be easily manufactured and utilized while requiring a minimum of material in order to conserve natural resources and reduce costs.

The invention which this document describes attacks the needle-stick problem at its area of greatest need: it succeeds in protecting the user from needlesticks incurred while preparing the item for disposal, it minimizes possible injury during use and it prevents hazards after disposal by shielding the needle.

The disclosed invention renders recapping after use unnecessary. Injuries such as those that occur when needle assemblies protrude from the openings of trash containers are also eliminated. The needle, even after disposal, is enclosed in the syringe tube which acts as a protective shield. This is especially important since, despite strict safety guidelines, needle assemblies themselves are often disposed of improperly, posing a constant threat to housekeeping staff and others.

The disclosed invention has a number of improvements over similar inventions already patented. Very little space is left in the syringe of my invention for medication to remain after injection—unlike the Haber syringe which possesses no mechanism to expel medication from the recesses which remain after the plunger has been pushed upon.

My invention makes reassembly essentially impossible. Additionally, an attempt to deactivate the retracting mechanism on the syringe prior to use—for example by cutting off the plunger tip —would result in a waste of the medication or illegal substance the user would find undesirable.

Furthermore, if the thumb ring is included at the end of the plunger, the syringe can be used with only one hand; the free hand has no reason to come in proximity with the syringe, (other than, for example, to place a sterile patch over the point where the needle entered the skin to prevent backflow of blood from the patient from the channel formed by the needle). The plunger does not need to be twisted in order to engage the needle assembly as it does in other designs, enabling the user to keep his or her other hand away from the syringe, reducing the opportunity for accidental needlesticks. The optional finger grip or flange provides a point of leverage to simplify retraction of the syringe.

The disclosed invention describes a retractable syringe which reduces the extra steps needed to use it. It requires less assembly during manufacture and reduces the number of possible manufacturing defects due to a reduction in the number of separate parts, and thus can be provided at a lower cost. My invention is designed to permit use of standard needle cannulas in order to permit the selection of needles of different size and gauge, to simplify manufacturing, to increase acceptance of the product, and to reduce inventory and storage requirements of hospitals. The disclosed invention does not require assembly by the user prior to use, other than the placing of the needle fixture on the end of the syringe if it does not come already attached.

The securing means on most embodiments of my invention prevent blood splatter by smoothly and decceleratingly engaging. These smoothly connecting engagement means also permit the user to withdraw the needle into the syringe without first withdrawing the needle from the patient—thus eliminating the need for the needle ever to be completely exposed after injection.

The original, standard needle cap may optionally be inserted through the now open distal end of the syringe barrel and pushed into place covering the retracted needle, thus completely enclosing the needle and preventing any possible dripping from the end of the needle or possible needlesticks to children or to staff who come in contact with improperly disposed of syringes.

Two major obstacles need to be overcome in designing a non-reusable syringe. Firstly, the user should not be given control over whether or not the syringe can be re-used. For instance, even though they know that they should not, many doctors and other healthcare workers reuse syringes. AIDS epidemics occur in hospitals in some countries where there are insufficient medical supplies: there are not the needed syringes to medicate the patients, so syringes are reused resulting in cross-contamination. The doctors are aware of the problem but continue to reuse syringes anyway.

Secondly, the problem of designing a syringe that can not be reused is exacerbated by the proliferation of extremely cheap labor in some of these countries. Supposedly "non-reusable" syringes can be torn apart and reassembled. Improved designs must cause reassembly to be a futile process.

The described invention overcomes these obstacles while remaining simple and inexpensive. Medication is drawn up just as with a typical syringe. The plunger must, however, be given a slight extra push after most of the medication is expelled so that the proper dosage is given. If this is not done, expensive medication will be wasted. Considering the relatively low cost of the syringe as compared to the cost of medication ($60 per injection is common), and the importance of the patient receiving the correct dosage, the healthcare worker will have incentive to use the product correctly. Drug addicts find themselves in similar circumstances; drugs are expensive and waste is undesirable. When given the extra push, the rubber plunger tip becomes slightly compacted, exposing a greater portion of the plastic, cone-shaped taper at the plunger tip and permitting the taper to be inserted to fit securely in the female taper on the needle assembly. When the plunger is pulled back, towards the proximal end of the syringe, the needle assembly break-away tabs are broken and the needle assembly is free to be pulled back inside the syringe barrel. So that the needle can not accidentally be re-exposed, the plunger should be pulled back until the slots, tabs, threads or bands which are located on the needle assembly are snapped into the corresponding slots, tabs, threads or bands on the inside of the syringe barrel.

Once the break-away tabs that are used to hold the needle assembly in place are broken, the syringe can not be re-assembled. There is no longer any mechanism to hold the needle assembly in place at the end of the syringe. (The nature of the plastics used to make syringes is such that glue does not work effectively on them.) If an attempt is made to separate the plunger from the needle assembly once the two have been engaged, a small (optional) protuberance on the tip of the plunger taper will break off into the needle cannula or fluid channel. This small protuberance will plug the needle cannula or fluid channel and act to further discourage reassembly of the syringe.

The needle may be attached to the needle assembly either in a permanent manner (during manufacture) or by the usual method just prior to use. In areas where adequate supply of medical disposables remains a problem, the former is preferable so that the needle can not be removed from the end of the needle assembly for reuse on another syringe.

DESCRIPTION OF THE PREFERRED EMBODIMENTS

Figure 1:
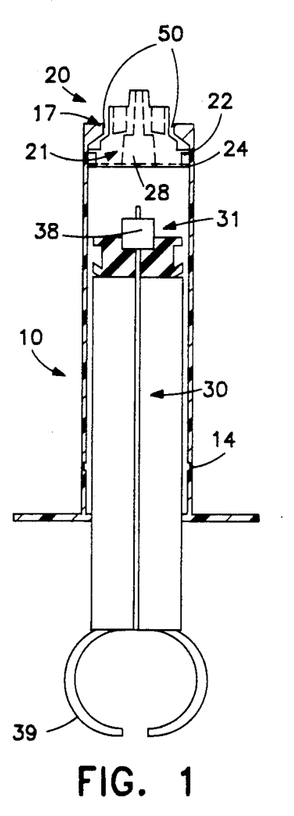
FIG. 1 shows a sectional view of the invention where the plunger has not yet been engaged with the needle assembly.
Figure 9:
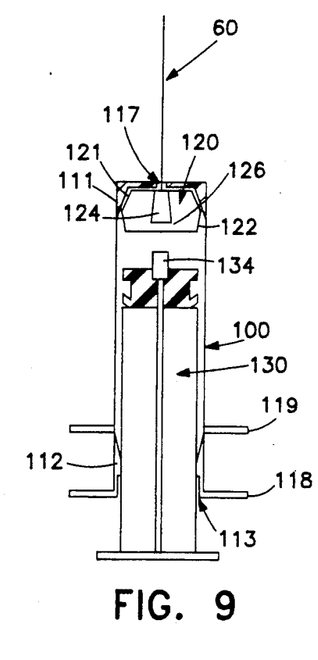
FIG. 9 shows a sectional view illustrating alternate embodiments of the needle assembly, the syringe barrel, and the plunger, before the needle assembly is engaged by the plunger.

FIG. 1 shows the invention, which consists of a hollow main cylindrical tube 10 which is adapted to have mounted on a needle assembly adaptation 50 at its distal end a standard needle fixture by means of threads, a morris taper, luer lock, or the like, or alternatively a fixed needle 60 (FIG. 9) will be embedded in the distal end of the needle assembly 120 (FIG. 9) as is common in a typical insulin syringe. Most embodiments of the invention are designed for use with a standard luer lock type needle fixture, such as those made by Becton-Dickinson and Sherwood Medical, but the needle assembly 20 (FIG. 1) may in any case be constructed with either the needle assembly adaptation 50 or the fixed needle 60 (FIG. 9).

Figure 2:
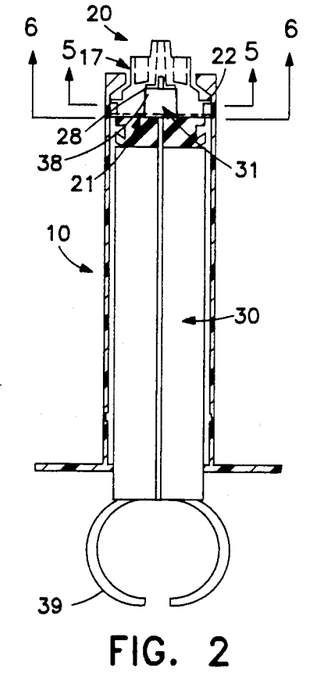
FIG. 2 shows a sectional view of the invention after the plunger has been compressed, thus allowing the plunger taper to engage the needle assembly.

With reference to FIG. 2, a needle assembly 20 is attached to the distal end of the syringe barrel 10 by means of break-away tabs 22 or similar means or by an adhesive or heat stake such that after the engageable means 31 that extends from the plunger 30 is firmly affixed to the proximal engageable means 21 of the needle assembly 20 and the plunger 30 is given a twist or pull, the needle assembly 20 will be disengaged from the syringe barrel 10. Optimally, the needle assembly 20 and syringe barrel 10 are cast as one piece during manufacture.

Figure 3:
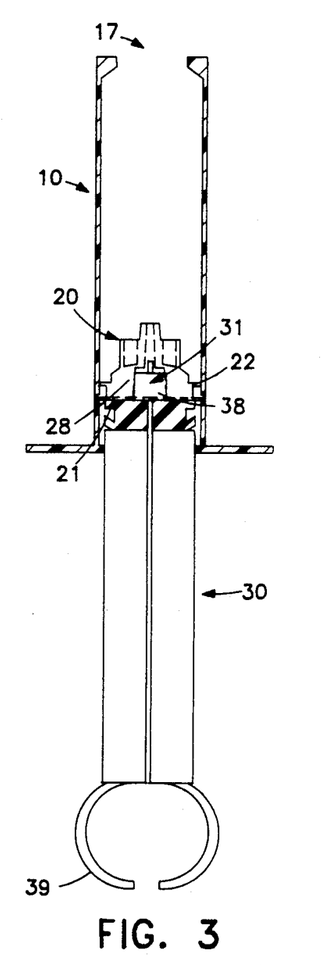
FIG. 3 shows a sectional view of the invention after the needle assembly has been fully retracted and the means at the proximal end of the syringe barrel have been engaged.

FIG. 3 shows the invention after the connection between the needle assembly 20 and the syringe barrel 10 is broken the needle assembly 20 is free to be moved axially along the syringe barrel 10, thereby allowing it to be drawn proximally into the syringe barrel 10 so that the needle is covered. The preferred embodiment has a thumb ring 39; it provides a leverage means for retracting the plunger 30 for one-handed use. The preferred embodiment has both the thumb ring 39 (FIGS. 1-3) and the extra finger-grip flange 119 (FIG. 9).

Description of Alternative Securing Means

Alternate embodiments of the invention utilize various means of securing the needle assembly 20 to the distal end of the syringe barrel 10. Some possible methods of attachment include: having either a recessed band on the inside of the syringe barrel which a raised ring, projection or tabs on the distal end of the plunger or needle assembly may be snapped into (or vice versa). Securing may be accomplished by using any of these types of locks or engageable means or by a combination of them.

The preferred embodiment of the syringe calls for a female tapered friction fit 28 on the inside of the needle assembly 20 which secures with a corresponding male friction fit band 38 on the plunger 30. The holding power of each securing means is such that the plunger taper 38 engages the needle assembly taper 28 with more strength than the engagement means that holds the needle assembly 20 in place at the distal end of the syringe barrel 10.

The proximal end of the syringe barrel 10 has either a recessed band 14 on the inside that a raised ring, projection or tabs on the plunger 30 or a raised ring 24, projection or tabs on the needle assembly 20 may be snapped into. Alternatively, the engaging means 24 on the plunger 30 or needle assembly 20 may be located on the syringe barrel 10 while the engaging means 14 on the syringe barrel 10 be located on the plunger 30, or needle assembly 20.

Figure 10:
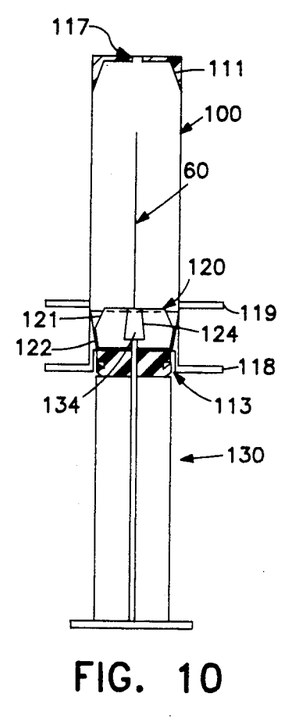
FIG. 10 shows a sectional view illustrating alternate embodiments of the needle assembly, the syringe barrel, and the plunger after the needle assembly has been fully retracted.

FIG. 9 and FIG. 10 show an alternate embodiment of the syringe with an extra finger-grip flange 119 that provides pushing leverage to retract the plunger 130 for one-handed use. FIG. 9 shows an alternate embodiment of the syringe that calls for an upper female tapered friction fit (morris taper) 111 on the inside of the syringe barrel 100 which secures with a corresponding upper male taper 121 on the exterior wall of the needle assembly 120. The plunger 130 can be easily inserted through the proximal opening 113 of the syringe barrel 100 during manufacture, but once it has been engaged with the needle assembly 120 and withdrawn inside the syringe barrel 100, the lower male taper 122 on the outside of the needle assembly mates with the lower female taper 112 on the syringe barrel 100, preventing the needle assembly 120 from being drawn through the opening 113 at the proximal end of the syringe barrel 100. These engaging lower tapers can hold with greater strength than do the tapers holding the plunger 130 into the needle assembly 120 so that the plunger 130 may be pulled out of the needle assembly 120 and pulled through the proximal opening 113 of the syringe barrel 100 so that it may be separately disposed of to save on disposable waste space requirements or so that it will be even more unlikely that the needle be accidentally forced back out of the distal opening 117 of the syringe barrel 100. This step is purely optional, since the needle assembly 120 is already in an essentially locking hold within the syringe barrel 100. When the user slides the needle assembly 120 proximally through the syringe barrel 100 to place it in the locking position at the proximal end of the syringe barrel 100, the tapers secure with each other with a decelerating effect which serves to prevent a sudden jarring of the device that may cause blood to splatter.

Figure 11:
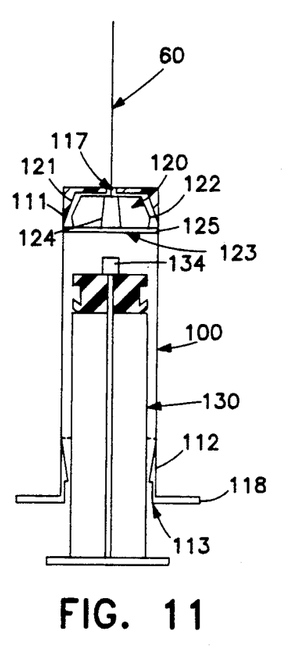
FIG. 11 shows a sectional view illustrating an alternate embodiment of the needle assembly where it is shown with a raised ring before the needle assembly is engaged by the plunger.

FIG. 11 shows an alternate embodiment in which a thin, slightly flexible circular flap 125 may extend radially outward from the proximal opening 123 of the needle assembly 120, just proximal to the lower male taper 122. It prevents flow of medication into the area between the inner walls of the syringe barrel 100 and the exterior walls of the needle assembly 120. It also makes an audible click when it passes over the most proximal portion of the lower female taper 112 on the proximal end of the syringe barrel 100 so that the user is given positive confirmation that the needle assembly 120 has been locked in place inside the syringe barre 100. It also prevents the needle assembly 120 from being pushed back down the syringe barrel 100 and emerging from the distal opening 117 of the syringe barrel 100. Please note that the distal portion of the needle assembly 120 may be configured similarly to the distal portion of the needle assembly 20 (FIG. 1) that has a needle assembly adaptation 50 (FIG. 1) to allow for attachment of a standard-type needle fixture. In such case, the distal opening of the syringe barrel 117 would need to be wider, similar to the distal syringe opening 17 (FIG. 1).

Figure 6:
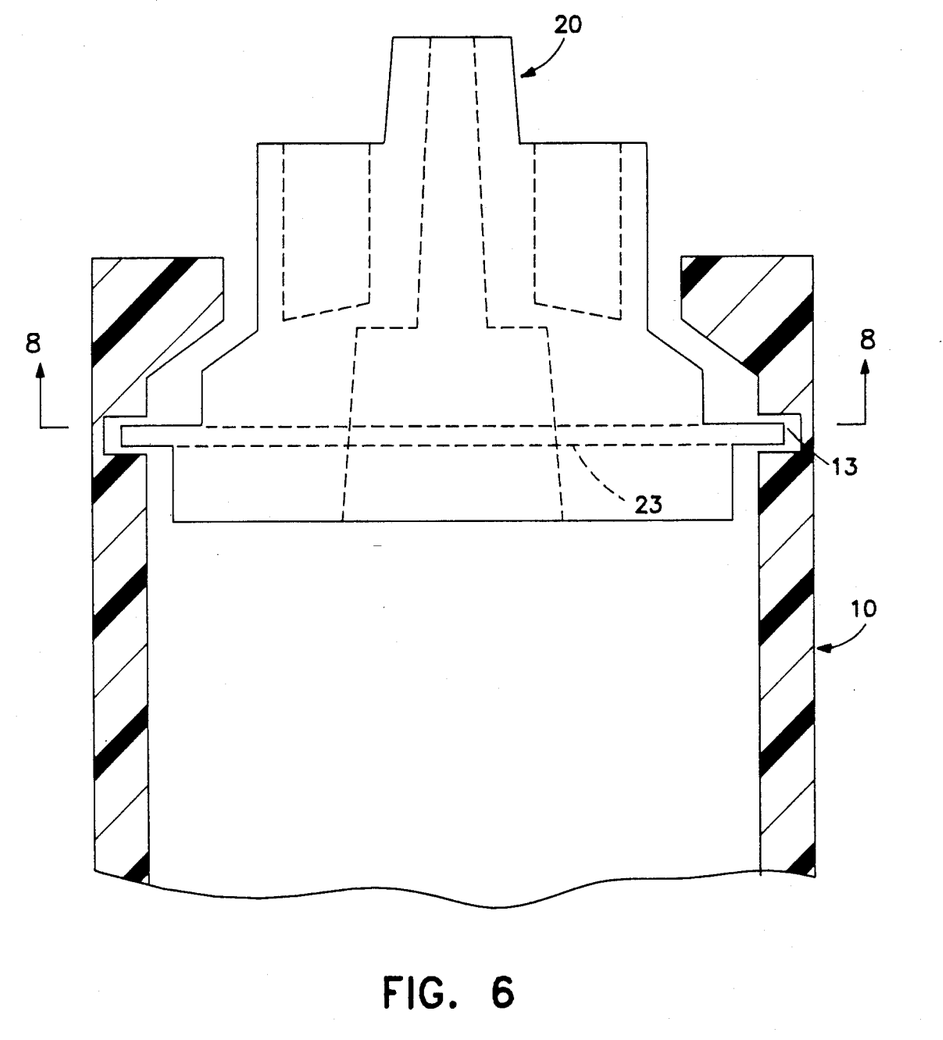
FIG. 6 shows an enlarged, fragmented view of an alternate embodiment of the needle assembly and syringe barrel as they appear prior to engagement by the plunger.
Figure 7:
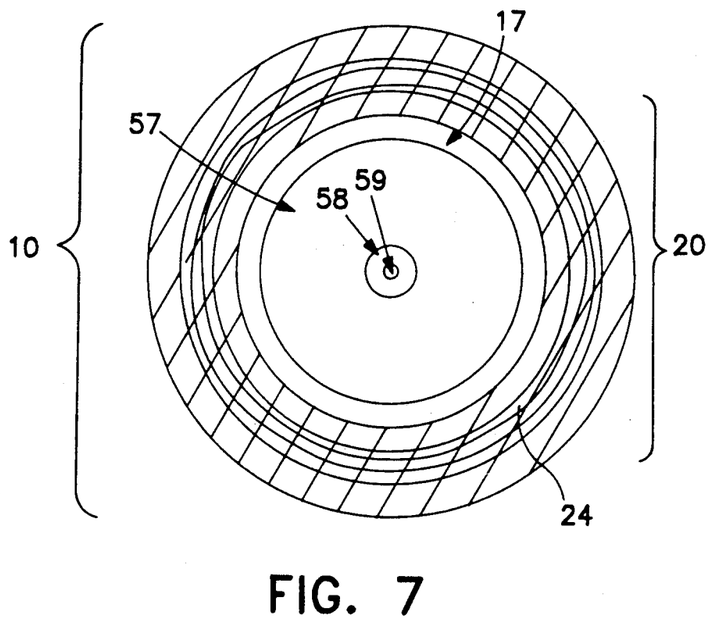
FIG. 7 shows a cross sectional view of the needle assembly and syringe barrel taken along line 8—8 of FIG. 6.

Another variation on securing the needle assembly 20 to the syringe barrel 10 is shown in FIG. 6. FIG. 6 shows an enlarged, fragmented view of this alternate embodiment as it appears prior to use. The needle assembly 20 is secured at the distal end of the syringe barrel 10 by a raised ring 23 that snaps into engagement with a recessed ring 13 on the syringe barrel 10. A cross sectional view taken at 8—8 of FIG. 6 is shown in FIG. 7.

Figure 12:
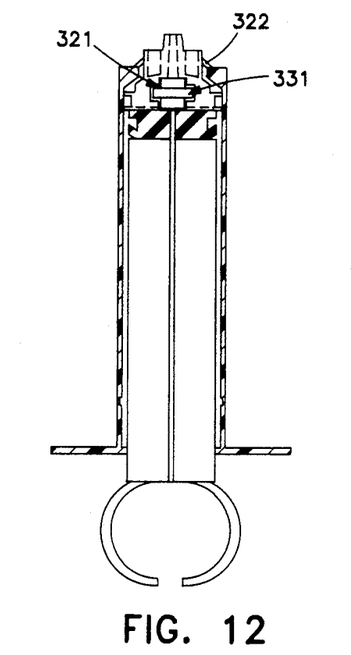
FIG. 12 shows a sectional view of an alternate embodiment of the invention showing an alternate location for the break-away tabs, and an alternate configuration of the engagement means of the needle assembly and plunger taper.

FIG. 12 shows a sectional view of an alternate embodiment of the invention showing an alternate location for the break-away tabs 322, and an alternate configuration of the engagement means of the needle assembly 321 and engagement means of the plunger 331 in the form of a pair of interlocking raised bands.

Figure 13:
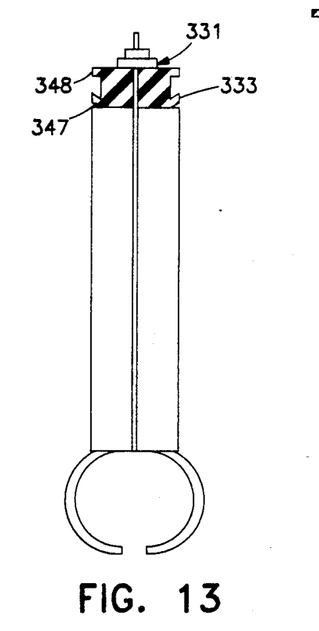
FIG. 13 a perspective view of an alternate embodiment of the plunger which has a raised ring as the engagement means, shown prior to compression of the rubber plunger tip.
Figure 14:
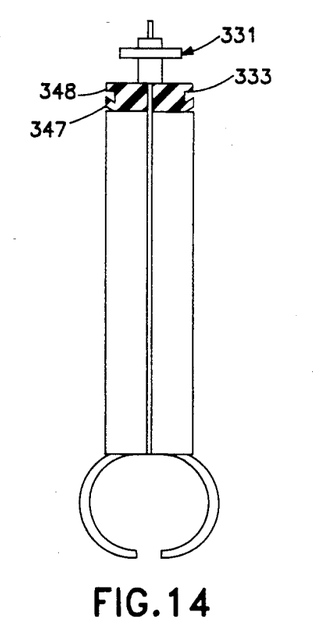
FIG. 14 a perspective view of an alternate embodiment of the plunger with a raised ring as the engagement means, shown after compression of the rubber plunger tip.

FIG. 12 and FIG. 14 show the plunger with a raised ring as the engagement means 331 prior to (FIG. 13) and after (FIG. 14) compression of the rubber plunger tip 333. The rubber plunger tip 333 in its preferred embodiment has slightly elongated lower flanges 347 and upper flanges 348 as well as lower flanges 347 which are angled more steeply in the distal direction than is standard so that the rubber plunger tip 333 offers less resistance when pulled in a proximal direction within the syringe barrel 10 to simplify use and to require less strength for one-handed use.

Figure 15:
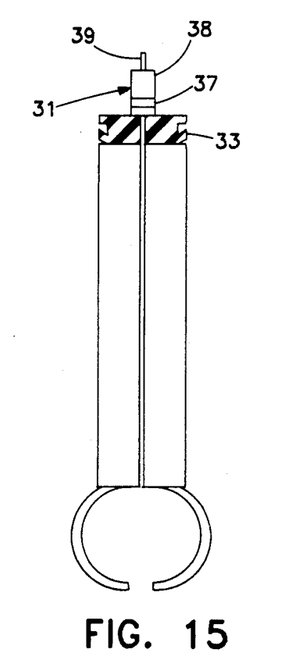
FIG. 15 shows a perspective view of the preferred embodiment of the plunger with a colored band for visual confirmation of the engagement of the plunger taper with the needle assembly.

FIG. 15 shows the preferred embodiment of the plunger with a colored band 37 located on the plunger engagement means 31. This colored band 37 is revealed only when the rubber plunger tip 33 is compressed. Thus, when the plunger engagement means 31 mates with the needle assembly engagement means 21 (FIG. 1) the colored band 37 is exposed to provide the user with visual confirmation of the engagement. In this case, the plunger engagement means 31 is shown as a male friction fit taper 38, although it may actually take a variety of different forms (e.g. threads, tabs, etc.)

FIG. 15 also shows the plunger tip projection 39 which is forced into a channel at the proximal end of the needle assembly 20 when the plunger 30 and needle assembly 20 become engaged. Any attempt to remove the plunger 30 (FIG. 1) from the needle assembly 20 (FIG. 1) will result in the plunger tip projection 39 (FIG. 15) breaking off from the plunger engagement means 31, where it will remain and block any further fluid flow.

In all cases any of the interlocking means (i.e. 21,31,22,24,14) may be replaced with any other interlocking means, such as screws and threads, morris tapers, friction fits, tabs and recessions, ridges and depressions, ratchet teeth, etc. Some interlocking means will of course be more practical or desirable than others, and I have illustrated the invention in some of its most preferred embodiments. These illustrations are not inclusive of all possible embodiments of the invention, and the spirit of this patent and its various intended optional features and uses should be taken into account.

Optional Oval Syringe Barrel

Figure 4:
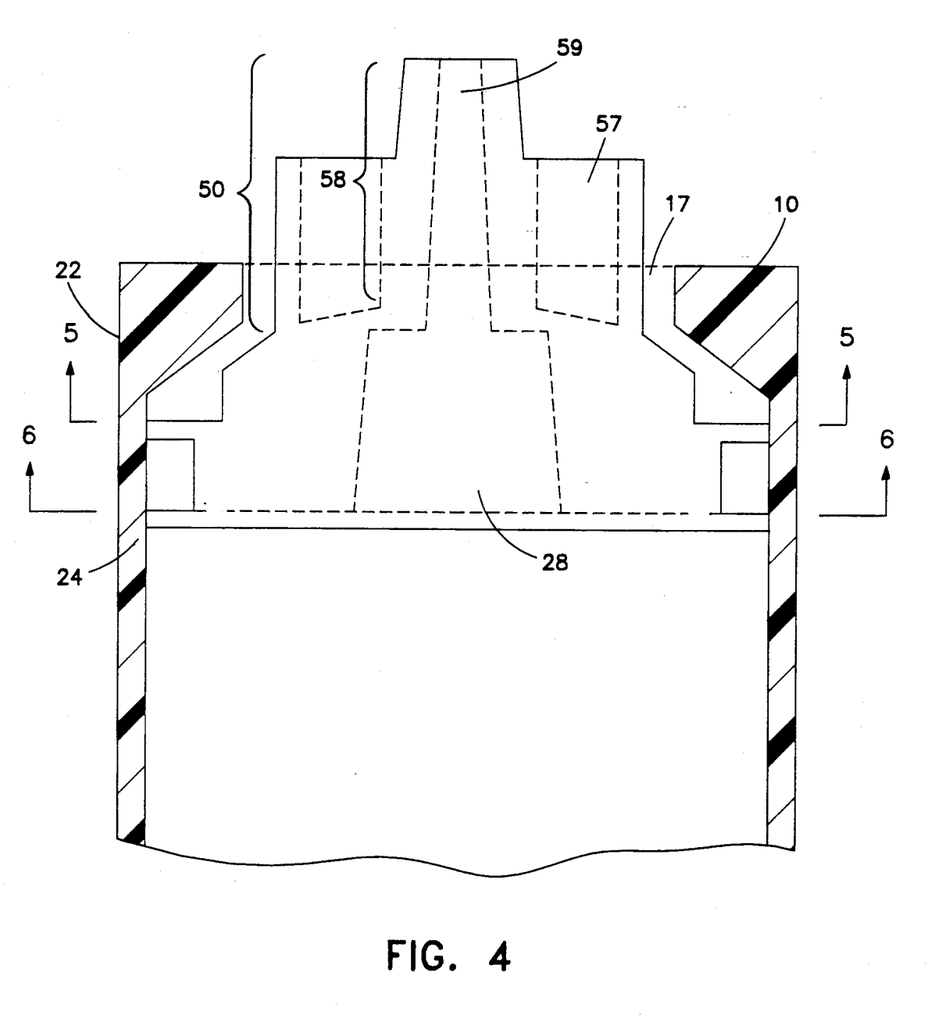
FIG. 4 shows an enlarged, fragmented view of the needle assembly as it appears prior to engagement with the plunger.
Figure 5:
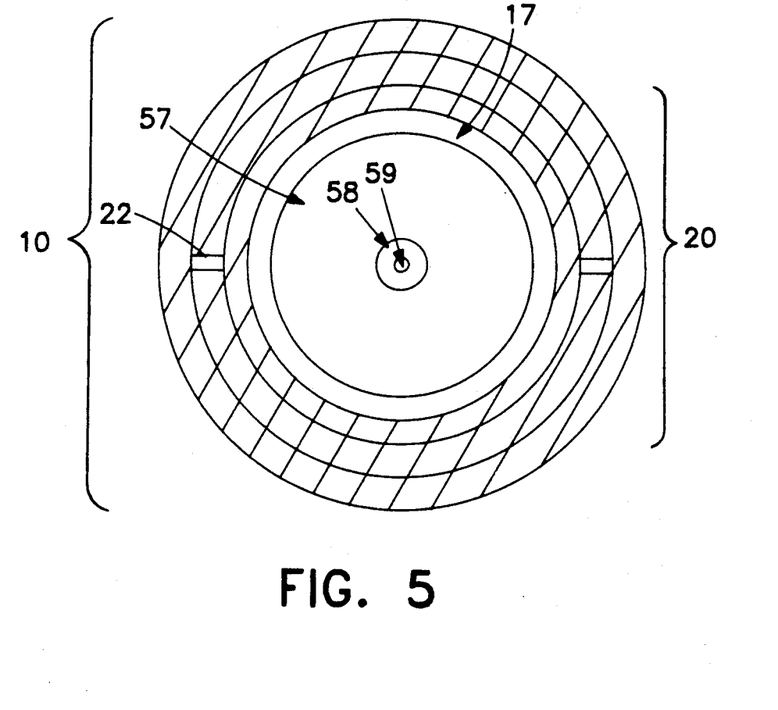
FIG. 5 shows a cross sectional view of the needle assembly and syringe barrel taken along line 5—5 of FIG. 2.
Figure 8:
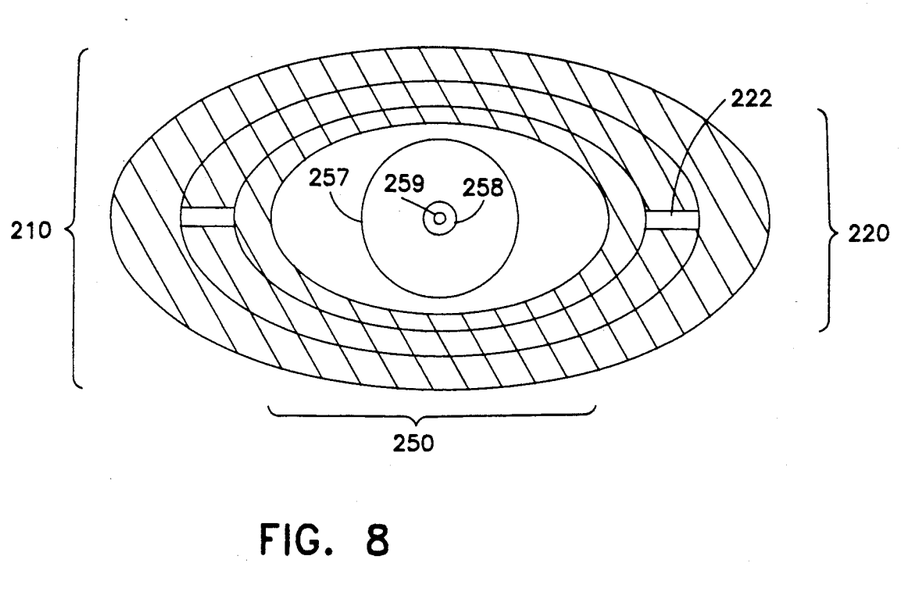
FIG. 8 shows a cross sectional view of an ovular embodiment of the invention with a standard needle adaptation, illustrating the relationship between the needle assembly and the syringe barrel as taken along line 5—5 of FIG. 2.

FIG. 8 shows an alternate embodiment of the invention which prevents the needle assembly 220 from twisting in relation to the syringe barrel 210. In sectional view this embodiment resembles FIG. 1 and parts 220, 210, 250, and 222 would appear as parts 20, 10, 50, and 22 of FIG. 1, respectively. This embodiment thereby permits the user to withdraw the needle directly into the syringe barrel 210 without having the bevel on the tip of the hypodermic needle rotating subcutaneously, causing possible tissue damage (however slight). However, it is often the case that, in order to prevent medication from seeping back up through the skin, the healthcare worker pushes on the skin to create a channel through the skin that is not quite straight, so that after withdrawal, when the tissue returns to its natural location, the channel that was formed by the entry of the needle is "filled in" with tissue that has returned to its natural position. Thus, this embodiment may be overly cautious. The syringe barrel 210 and needle assembly 220 have ovular instead of circular cross-sectional profiles. The ovular shapes prevent the tubes from twisting in relation to each other during use so that control of the product during use is improved. In an embodiment where friction fit tapers are used to secure the needle assembly in position at the distal end of the syringe this configuration may be undesirable, since the simplest way to disengage a friction fit is often to twist the parts while gently pushing or pulling them apart (a motion which the oval shape of the syringe barrel 210 and needle assembly 220 would prevent). The shapes of the other parts of the syringe barrel and the needle assembly would not necessarily need to be ovular in shape but could maintain their circular profiles. For instance, the needle-fixture adaptation 250 would still have a circular taper 258 and fluid channel 259 and circular threaded opening 257 (in an enlarged, fragmented view, parts 257.258, and 259 would appear as parts 57,58, and 59, of FIG. 4, respectively).

Audio and/or Visual Confirmation of Successful Securing; Measurement Markings Confirmation of the successful engagement of the plunger tip engageable means 31 with the needle assembly engageable means 21 may be given by a small click made by the movement of the pieces against each other. In one embodiment, FIG. 9 for example, confirmation of the successful engagement of the plunger taper 134 with the needle assembly female taper 124 is given by a small click made by the tabs 126 on the inner, proximal end of the female taper 124 on the needle assembly 120 as the widest part of the male taper 134 slips past them.

Visual confirmation may be given by a brightly colored band 37 (FIG. 15) on the proximal end of the male taper 38 which is revealed when the rubber-like plunger tip 33 is compressed. The syringe barrel 10 (FIG. 1) is of a transparent material so that the marking may be easily seen as well as the contents of the syringe (e.g. so that medication levels may be seen, so that blood flashback may be seen, so that air bubbles are visible, etc.). Measurement markings or securing position indicators can be made on the syringe barrel 10 itself to further simplify use of the product.

Optional Enclosing Cap

Finally, an optional cap may be inserted into the end(s) of the shield to completely enclose the needle and to prevent reuse of the syringe (by drug abusers, etc.). The cap is such that it can easily be inserted yet is essentially irremovable (for instance an alternate embodiment of the syringe barrel could have a keyhole-shaped opening at the distal opening 17 which would allow the user to fit the key-shaped portion of the cap through it; once the cap has been pushed all the wa inside the distal opening 17 (FIG. 1) there would be no way for it to be aligned correctly to fit back out through the key shape.)

It is to be understood that the forms of the invention herewith shown and described are to be taken as preferred examples of the same, and that various changes in the shape, size and arrangement of parts may be resorted to, without departing from the spirit of the invention or scope of the subjoined claims.

In brief, the invention is a syringe with a retractable needle assembly 20. The syringe is aspirated with medication in the usual manner, and the injection is administered to the patient in the usual manner. After the plunger 30 is pushed to the end of the barrel to eject the medication, a slight extra push is given to the plunger 30. This extra push compresses the rubber-like plunger tip 33 (FIG. 15), exposing the balance of a plunger engageable means 31 (FIG. 1) which partially extends from the rubber-like plunger tip 33. The plunger engageable means 31 expels any remaining medication and then engages with the needle assembly engageable means 21. The plunger 30 is then drawn back, pulling the needle assembly 20 inside the barrel 10 where it is locked in place at the proximal end by a pair of engaging means. The syringe, with its various embodiments, may be adapted to meet a number of different needs. It may be made with an attached needle or with a fixture which a standard-type needle may be affixed to. It may be made for use by medical personnel who practice proper administration and disposal of syringes to help protect them from needlesticks, or it may have further adaptations for use by those who do not practice proper disposal to prevent the syringe from being reused. Furthermore, the syringe can be made for one-handed use.

What is claimed is:

1. In a syringe containing (1) a barrel having an elongated cavity, a longitudinal axis through the elongated cavity, an open proximal end, a distal end, an inner wall surface, and an outer wall surface and (2) a plunger capable of moving reciprocally and axially in the barrel, having an outer wall surface adapted to slidably engage the inner wall surface of the barrel, a proximal end, and a distal end, the improvement consisting essentially of:
   a) a needle assembly removably mounted on the distal end of the barrel, which needle assembly has a lateral surface, a proximal end, a distal end, and a central channel,
   b) the proximal end of the needle assembly and the distal end of the plunger have a corresponding engaging means selected from the group consisting of corresponding raised ring and recessed band, threads, a friction fit provided by corresponding male and female tapers, and corresponding raised tab and recessed tab wherein the engaging means of the plunger can fixedly engage the engaging means of the needle assembly so that, following engagement, when the plunger is retracted toward the proximal end of the barrel, the needle assembly is separated from the distal end of the barrel and retracted into the barrel, and
   c) corresponding engaging means situated on 1) the lateral surface of the needle assembly or 2) the outer wall surface of the plunger at the distal end of the plunger and the inner surface of the barrel near the proximal end of the barrel such that when the needle assembly is retracted inside the barrel, the needle assembly cannot be withdrawn from the proximal end of the barrel, but becomes locked to the inner surface of the barrel near the proximal end thereof.

2. The syringe as described in claim 1, wherein the needle assembly is removably mounted on the barrel by means of break-away tabs, a corresponding raised ring and recessed band, threads, or a friction fit provided by corresponding male and female tapers, or corresponding raised tab and recessed tab.

3. The syringe as described in claim 1, wherein the retracted needle assembly is secured to the inner wall surface of the barrel by a corresponding raised ring and recessed band, threads, or a friction fit provided by corresponding male and female tapers, or corresponding raised tab and recessed tab.

4. The syringe as described in claim 1, wherein the barrel, the needle assembly and the plunger are ovular in shape.

5. The syringe as described in claim 1, wherein the proximal end of the plunger contains a thumb ring.

6. The syringe as described in claim 1, wherein finger-grip flanges or finger-grip rings are mounted near the proximal end of the barrel.

7. The syringe as described in claim 1, wherein the distal end of the plunger contains a compressible tip surrounding the engaging means and is mounted on the plunger such that in the uncompressed state of the compressible tip the engaging means partially projects from the compressible tip, while in the compressed state of the compressible tip the engaging means is fully exposed and is capable of engaging the engaging means of the needle assembly.

8. The syringe as described in claim 7 wherein the proximal end of the engaging means located at the distal end of the plunger is colored, thereby providing visual confirmation of a fit between the plunger engaging means and the needle assembly engaging means when the compressible tip is in the compressed state.

9. The syringe as described in claim 1, wherein the distal end of the plunger contains a tip surrounding the engaging means, which tip has slightly elongated lower flanges and upper flanges, the lower flanges being angled steeply in the distal direction so that the tip offers less resistance when pulled in a proximal direction within the syringe barrel.

10. The syringe as described in claim 1, wherein the plunger engaging means contains a plunger tip projection which is forced into the channel at the proximal end of the needle assembly when the needle assembly engagement means and the plunger engagement means become engaged and which breaks off if the plunger is forced out of engagement with the needle assembly.

11. The syringe as described in claim 1, wherein the needle assembly has an adaptation for a standard needle.

12. The syringe as described in claim 1, wherein 1) the inside wall of the barrel, at the distal end thereof, contains a distal female taper which secures with a corresponding distal male taper on the exterior wall of the needle assembly to removably mount the needle assembly to the barrel and 2) the inside wall of the barrel, at the proximal end thereof, contains a proximal female taper which secures with a corresponding proximal male taper on the exterior wall of the needle assembly to secure a retracted needle assembly to the barrel and prevent the needle assembly from being drawn through the proximal end of the barrel while allowing the plunger to separate from the needle assembly and be withdrawn through the proximal end of the barrel.

13. A syringe as defined in claim 12, wherein a flexible circular flap extends radially outward from the proximal end of the needle assembly to the inner wall surface of the barrel.

* * * * *